United States Patent [19]

Ornstein et al.

[11] 4,257,346

[45] Mar. 24, 1981

[54] APPARATUS FOR MOUNTING TISSUE SECTIONS WITH AN U.V. LIGHT CURABLE MOUNTING MEDIUM

[75] Inventors: Leonard Ornstein, White Plains; Hazel E. Williams, Ossining; Julius Intraub, Plainview, all of N.Y.

[73] Assignee: Technicon Instruments Corp., Tarrytown, N.Y.

[21] Appl. No.: 910,411

[22] Filed: May 30, 1978

Related U.S. Application Data

[62] Division of Ser. No. 749,557, Dec. 10, 1976, Pat. No. 4,120,991.

[51] Int. Cl.³ .......................... B05C 5/00; G01N 1/28
[52] U.S. Cl. .................................... 118/641; 118/206; 118/257; 118/684
[58] Field of Search ................. 424/3; 8/94.11; 427/2, 427/4; 350/92; 156/57; 118/257, 641, 206, 642, 684

[56] References Cited

U.S. PATENT DOCUMENTS

| | | | |
|---|---|---|---|
| 3,498,860 | 3/1970 | Pickett | 424/3 X |
| 3,629,036 | 12/1971 | Isaacson | 156/247 X |
| 3,891,327 | 6/1975 | Welch | 350/92 X |
| 4,120,262 | 10/1978 | Adler et al. | 118/257 X |

*Primary Examiner*—John P. McIntosh
*Attorney, Agent, or Firm*—S. P. Tedesco

[57] ABSTRACT

Apparatus for permanently and protectively mounting "wet" thin sections of biological specimens on microscope slides, wherein each specimen is initially bathed in a low-volatile solvent containing a low concentration of first polymerizable material. Such solvent is allowed to evaporate, whereby the liquid polymerizable material permeates and protects the specimen. Following solvent evaporation, a second polymerizable material is layered over the specimen. Preferably, the first and second polymerizable materials comprise a mixture of low-volatility, low-viscosity, liquid acrylic reactomers and a U.V. light-sensitive catalyst system. A conventional cover slip or other planar transparent member can be positioned over the polymerizable materials, and the same are polymerized by exposure to U.V. radiation. The first and second now-polymerized materials encapsulate the specimen on the microscope slide, become integral and completely hardened and are fully devoid of any solvent. The microscope slide is immediately available for examination.

4 Claims, 2 Drawing Figures

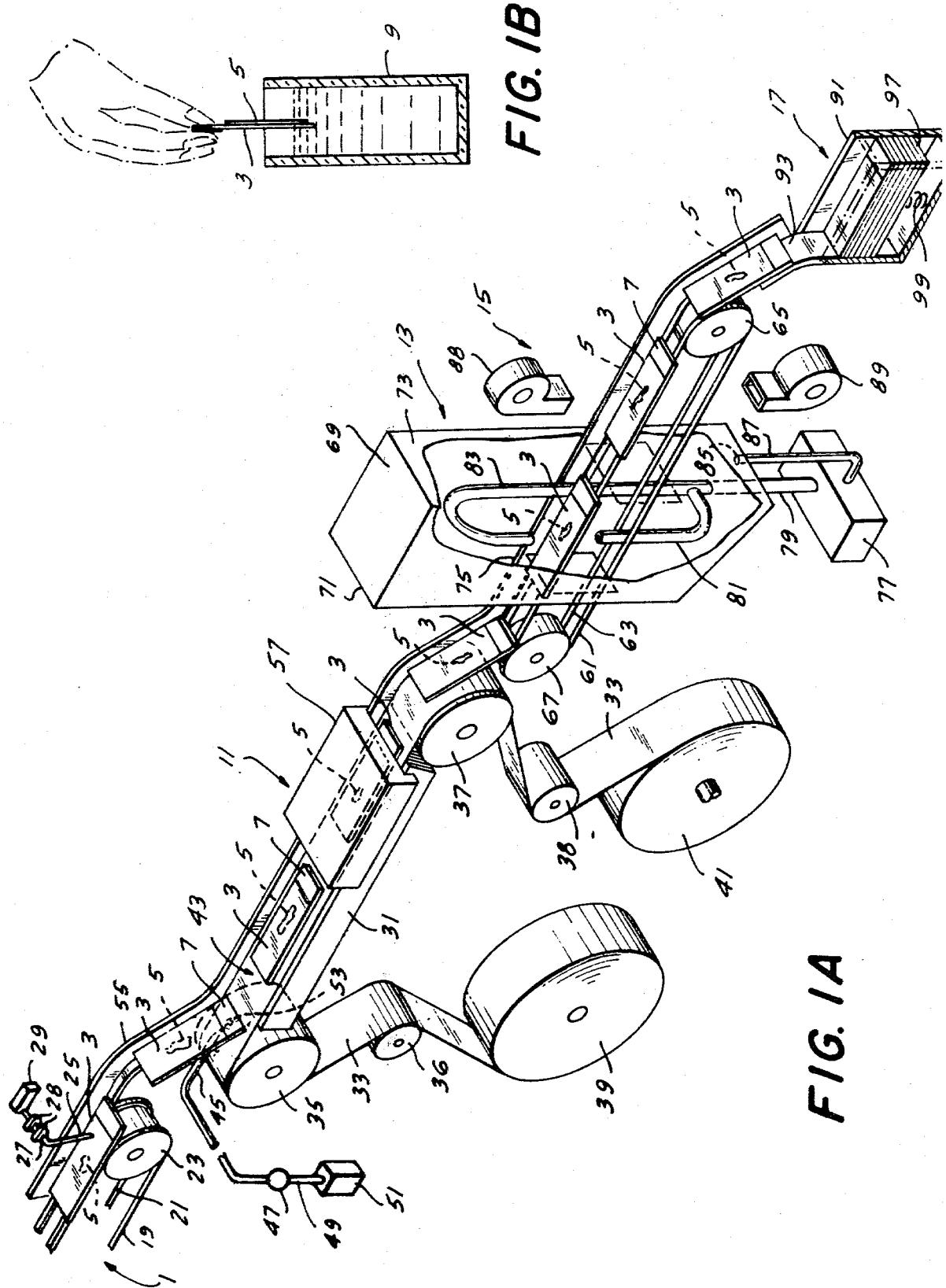

APPARATUS FOR MOUNTING TISSUE SECTIONS WITH AN U.V. LIGHT CURABLE MOUNTING MEDIUM

RELATED APPLICATION

This application is a divisional application of Ser. No. 749,557, filed Dec. 10, 1976, now U.S. Pat. No. 4,120,991, issued Oct. 17, 1978.

BACKGROUND OF THE INVENTION

1. Field of the Invention

This invention relates to apparatus for providing permanent, optically clear preparations of biological specimens on microscope slides for cytologic, histologic and pathologic study.

2. DESCRIPTION OF THE PRIOR ART

It is common practice in the medical field to provide thin sections of biological specimens on glass slides for microscopic study, such sections have been stained (to enhance definition for examination), dehydrated and subjected to a mounting process. Generally, such mounting process encloses each individual specimen in a medium supported on a microscope slide and wherein it is preserved indefinitely. The present trend is to use a solvent solution of hard synthetic resins as the mounting medium, or mountant. Such resins are chosen so that they (1) do not cause the stains with which the specimens are treated to fade, (2) yellow minimally with age, and (3) have refractive indices after drying which closely approximate the average refractive index of tissues (1.530–1.570). If a mountant having a refractive index close to that of the specimen is used, an almost perfect transparency can be achieved. A β-pinene resin is often used as mountant. For a listing of other available mountants, reference is made to table 5–1 on page 98 of Histopathic Technique and Practical Histo-chemistry by R. D. Lillie, McGraw-Hill Book Company, New York (1965).

Generally, the mountant is dissolved in a quantity of solvent, to provide proper viscosity for the convenient dispensing of a controlled volume thereof over the specimen. To provide a planar upper surface, necessary for proper microscopic examination, it is common practice to apply a glass cover slip over the dispensed mountant while still in liquid form. To remove all solvent, the presence of which can interfere with the examination process, the slides are subjected to an extended drying process, which may require several days or more. During such process, the slides are placed in a horizontal position, and sometimes within a warm environment, to facilitate solvent evaporation. Such solvent evaporation is essential to (1) harden the mountant, (2) seal the cover slip, so as to permit handling of the slides, and (3) avoid optical interference by the low refractive index of residual solvent during examination.

At the present time, the mounting and drying processes are done manually in the laboratory. Commonly, after removing the slide from the so-called clearing solution and quickly draining the same, one to several drops of mountant are deposited by the technician over the specimen. The quantity of such mountant should be sufficient to just occupy the space between the cover slip, when applied, and the specimen. Immediately, the cover slip is carefully positioned by the technician by being lowered gently upon the mountant. The technique contemplates that one side of the cover slip is placed on the mountant, which is then released to push before it a portion of the mountant as it descends into proper position. Often, the cover slip requires some adjustment by the technician, so as to achieve a thin even film of mountant, to eliminate any entrapped air bubbles from beneath the cover slip, and to properly center the cover slip over the specimen. Any surplus of mountant expressed beyond the cover slip should be quickly and carefully removed, for example, with absorbent paper, by the technician.

The most common difficulties encountered in the mounting of specimens are (1) a delayed application of the mountant after the specimen is removed from the clearing agent allows the drying of the specimen, whereby some deterioration of the tissue structure results, (2) the amount of mountant is inappropriate, whereby the resultant film beneath the cover slip is too thick or too thin or the plane of the cover slip is not parallel with that of the microscope slide, and (3) too rapid or careless application of the cover slip traps air bubbles, which become increasingly more difficult to release as the mountant begins to dry.

The prior art procedures, which have been only briefly described, have well-recognized disadvantages, among which are:

1. Since the specimen can be damaged if allowed to dry, the mountant must be carefully and quickly applied by the technician.

2. Since the solvent in the mountant has a low index of refraction and diffuses only slowly out from under the cover slip during the drying process, the mountant is generally prepared with a minimum of solvent, usually sufficient only to allow convenient dispensing. However, if the placement of the cover slip is delayed, the surface of the mountant can begin to dry, which tends to increase the probability of trapping air bubbles under the cover slip. Accordingly, the cover slip must be both carefully and quickly positioned on the mountant.

3. If an excess of mountant is dispensed, such excess must be expressed beyond the edges of the cover slip. Adequate removal of such excess may require the use of an appropriate solvent, which might flow under the cover slip and remove underlying mountant, ultimately leaving air spaces which would interfere with the examination.

4. During the drying process, the slide must be set aside on a flat horizontal surface for a considerable period. Tilting of the slide during such process often causes the cover slip to slide off the tissue section. Also, since the edges of the mountant extend slightly beyond the periphery of the cover slip and diffusion of solvent from under such cover slip keeps such edges sticky, the slides cannot be stacked for efficient storage until the drying process is complete.

5. Even after a prolonged drying process, a minimum quantity of solvent remains under the central portion of the cover slip. Inasmuch as the solvent has a relatively low refractive index, the optical properties of the slide remain sub-optimal for a long time period.

6. If the tissue specimen should have a high point, a thick layer of mounting medium would be present under the cover slip. Accordingly, the drying process would be delayed and considerable shrinkage of the mounting medium would result as the solvent evaporates. Such shrinkage often occurs unevenly and locally, such as to create an air space under the cover slip which would obscure tissue detail.

OBJECTS OF THE INVENTION

An object of the present invention is to provide improved method and apparatus for mounting a tissue specimen, whereby the total processing time is very significantly reduced.

An additional object of this invention is to provide improved method and apparatus for mounting tissue specimens, whereby the prolonged drying process of prior art procedures is substantially eliminated, such that mechanically stable and dry mounted specimens are immediately available for examination.

Another object of this invention is to provide apparatus and method for immediately achieving optically clear and stable preparations of such specimens having indices of refraction closely approximating that of the specimen.

SUMMARY OF THE INVENTION

According to the present invention, a mountant comprising a mixture of low-volatility, low-viscosity, liquid acrylic reactomers, and an ultra-violet-light sensitive catalyst system is employed as the final encapsulation medium. Such mountant remains free-flowing until polymerized, whereupon it becomes a hardened, optically clear, solvent-impermeable and solvent-proof medium fully encapsulating the specimen. Such mountant does not cause the stains to fade and remains colorless and clear. The acrylic reactomers are particularly chosen to provide a final refractive index, after polymerization, between 1.530–1.570 (typically 1.550) to match that of the specimen. As is known, refractive index can be controlled, for example, by mixing two components having lower and higher refractive indices, respectively, and varying proportions, to achieve any intermediate refractive index.

As the dehydrated section must not be permitted to dry, the specimen-carrying slide is initially typically bathed in a low-viscosity, high volatility solvent solution of a low concentration of mountant. Such mountant may be either of the same material as the final encapsulation medium or an equivalent compatible material, to yield a same refractive index after polymerization. The slide is then drained. In contrast to standard or classical procedures, the solvent is allowed to completely evaporate, such that a very thin protective layer of solvent-free but liquid mountant remains over the specimen at this time to prevent drying. As the components of such mountant have an extremely low-volatility, they do not evaporate significantly. Rather, the tissue remains wet and permeated with the mountant. When the solvent has been evaporated, usually within one minute, an appropriate final volume, or layer, of the final encapsulating mountant is placed over the "wet" section and the cover slip is leisurely applied. The mountant is then exposed through the cover slip (or microscope slide) to U. V. radiation, typically from a low-wattage flourescent black-light lamp, to effect the polymerization thereof within one minute. Accordingly, successively applied layers of the mountant under the cover slip become integral and completely hardened. Also, the resultant mountant is fully devoid of any solvent which might interfere with the examination process, which can be immediately effected.

Also, an advantage of the present invention is that the small excess of mountant expressed from beneath the cover slip remains liquid, since it remains exposed to oxygen in the atmosphere, which acts as a polymerization inhibitor to thin layers of reactomers, as is well known. Accordingly, the microscope slide can be thoroughly washed with an appropriate solvent to remove excess liquid mountant expressed beyond the cover slip without affecting the polymerized mountant or can be wiped dry by the technician, so as to be immediately ready for examination or stacked for storage.

The present invention, therefore, generally contemplates the dual application of mountant over the specimen. The first application of mountant is effected with a highly volatile solvent solution of a low concentration of mountant immediately following removal of the slide from the clearing solvent and the second application is effected with pure mountant. Each such mountant is polymerizable, preferably sensitive to U. V. light, and compatible with the other. Regarding the first application, the solvent is allowed to evaporate completely from the uncovered mountant, whereby the specimen is fully protected from drying and permeated by the mountant, which is still in liquid form. During the second application, any additional necessary volume of mountant is applied over the first layer of mountant, followed by a cover slip, and polymerization of both layers effected concurrently. Accordingly, the individually applied layers of mountant become integral and are fully devoid of all solvent, so as to be capable after polymerization of being handled immediately for examination.

BRIEF DESCRIPTION OF THE DRAWINGS

FIG. 1A is an isometric view of the apparatus for mounting tissue specimens on microscope slides and embodying the invention;

FIG. 1B is a sectional view of ancillary apparatus to be used in conjunction with the apparatus of FIG. 1A.

DETAILED DESCRIPTION OF THE PREFERRED EMBODIMENT

Referring now to the drawings, an apparatus is illustrated in FIG. 1A, which embodies the method of the present invention. Such apparatus comprises a feeding arrangement 1 for successively delivering microscope slides 3, each supporting a tissue specimen 5, which is to be mounted for examination. Each microscope slide 3 includes a label portion 7, identifying the corresponding tissue specimen 5. Initially, each tissue specimen 5 has been positioned on a corresponding microscope slide 3 by conventional techniques, dried, deparaffined, hydrated, stained, dehydrated, cleared and then bathed in a liquid comprising a low concentration (1% to 25%) solution of mountant in a low-viscosity, high-volatility solvent. As illustrated in FIG. 1b, such liquid may be contained within a container 9, into which each microscope slide 3 would be immersed by the technician, immediately following the conventional clearing step, whereby the specimen is left wet with a volatile solvent, e.g., xylene. The liquid in container 9 might consist, for example, of xylene, toluene, or Freon TF, and an appropriate mountant. Bathing in container 9 provides, after removal, a thin layer of liquid over tissue specimen 5. The solvent in such liquid is allowed to completely evaporate, such that a very thin protective layer of solvent-free liquid mountant remains over both surfaces of the microscope slide. At this time, the tissue specimen 5 remains wetted and permeated throughout with the mountant. Each microscope slide 3 is positioned, in turn, on the feeding arrangement 1, so as to be passed successively to a layering unit 11.

Layering unit 11 functions to provide a second layer of the same mountant over tissue specimen 5, which mountant comprises a mixture of low-volatility, low-viscosity liquid acrylic reactomers such as monomers or oligomers of methacrylates, acrylates and vinyls and, also, a catalyst sensitive U.V. light, such as benzoin, benzoin ether, acetophenones, or Michler's Ketone. Additionally, the layering unit 11 functions to expose the layers of mountant to U.V. radiation peaked near the absorption maximum of the catalyst, whereby both layers are polymerized in on-line fashion. Subsequently, microscope slides 3 are passed, in turn, through a wash station 13, wherein the surfaces of each slide are washed to remove all portions of unpolymerized mountant remaining thereon. The washed microscope slides 3 are subsequently passed through a drying station 15 to accelerate evaporation of the washing liquid and subsequently to a stacker arrangement 17 for accumulating the fully-processed microscope slides 3, which are immediately available for examination. The total processing time required for completely mounting, washing and drying each microscope slide from the time introduced into layering unit 11 is approximately two minutes.

To more particularly describe the apparatus, each microscope slide 3 supporting a tissue specimen 5 and after manual immersion into and removal from container 9 is manually positioned by the technician onto feeding arrangement 1. While the bathing and positioning of the microscope slides has been described as effected manually, the present invention contemplates that structure for effecting the same in on-line fashion could be included as an integral part of the feeding arrangement 1. Feeding arrangement 1, only a portion of which is illustrated in FIG. 1A., comprises a parallel belt assembly comprising endless belts 19 and 21 and a suitably driven roller 23. Preferably, roller 23 along with a non-illustrated associated idler roller are recessed along the central surface portions to define shoulders upon which belts 19 and 21, respectively, are trained. Each microscope slide 3 is positioned on parallel belts 19 and 21, such that the tissue specimen 5 is located on the lower surface and disposed between such belts. Additionally, a pair of parallel guides 55, only one of which is shown, are positioned in near adjacency to belts 19 and 21 to ensure the proper positioning and orientation of each slide 3 thereon.

The passage of each microscope slide 3 along feeding arrangement 1 is sensed by means of a feeler arrangement which initiates operation of the apparatus with respect to processing of each such slide. Such feeler arrangement comprises a finger 25 mounted at one end of the rotating shaft 27. Shaft 27 is supported by bearings 28, such that finger 25 extends downward through the spacing between belts 19 and 21. The passage of a microscope slide 3 forces finger 25 to rotate shaft 27 which, in turn, operates microswitch 29.

Microswitch 29, when operated, initiates operation of the layering unit 11, as now described. Layering unit 11 comprises a horizontal platen, or support, member 31 disposed betwen idler rollers 35 and 37 and over which a continuous optically smooth ribbon 33 is drawn. Ribbon 33 is supplied from supply spool 39 and advanced by means of a take-up spool 41. Appropriate tension is maintained on ribbon 33 by idler rollers 36 and 38. Operation of the take-up spool 41 is initiated by operation of microswitch 29. Additionally, operation of the microswitch 29 initiates dispensing of mountant over the upper surface 43 of ribbon 33 for ultimate encapsulation of the tissue specimen 5 on the microscope slide 3 which is then being advanced to layering unit 11.

A dispenser 45 is positioned over and adjacent to the upper surface 43 of ribbon 33 and connected through a valve 47 and along conduit 49 to a pressurized source 51 of mountant. Valve 47 is operated by the closure of microswitch 29, with appropriate delay, to dispense a continuous bead 53 of mountant onto surface 43 of ribbon 33. The length of bead 53 should preferably be as long as the length of a microscope slide. Also, the mountant is dispensed at a rate to ultimately form a thin layer thereof between the opposing surfaces of the microscope slide 3 and ribbon 33, as hereinafter described.

As illustrated, each microscope slide 3, in turn, is passed from over the belts 19 and 21 of feeding arrangement 1 onto a first ramp arrangement comprising guides 55, only one of which is illustrated. Guides 55 are formed in mirrored L-shaped fashion to define a shoulder portion, for supporting microscope slide 3 and a guide portion for orienting such slide during passage. The inclination of guides 55 is such as to gravitationally feed each microscope slide 3 onto ribbon 33. The advance of ribbon 33 causes the microscope slide 3 to be layered over the bead 53 of mountant dispensed on the surface of such ribbon. As ribbon 33 is initially contacted by the leading end of each microscope slide 3, the layering of such slide expresses mountant to the edges and ensures that the same is spread between the entire opposing surfaces of the slide and ribbon. In this connection, the ribbon 33 functions as would the cover slip in the conventional technique. The volume of mountant dispensed upon ribbon 33 should be only slightly in excess of that required to ensure the formation of a continuous layer of mountant between such opposing surfaces. The positive spreading of mountant between the opposing surfaces of the microscope slide 3 and ribbon 33 and the planarity of the ribbon 33 ensure that any surface irregularities in the first layer of mountant are filled and that the surface of the resulting, or final, layer of mountant is optically smooth and planar.

As ribbon 33 is further advanced by the action of take-up spool 41, the microscope slide 3 is carried through a chamber 57, which includes an appropriate black-light lamp, which is not illustrated, for polymerizing the mountant layers between opposing surfaces of the microscope slide 3 and ribbon 33. Such lamp may be energized by microswitch 29 concurrently with the energization of take-up spool 41. In chamber 57, the mountant layers disposed between ribbon 33 and slide 3 are fully polymerized.

As illustrated, the direction of ribbon 33 after passing over roller 37 is reversed, because of the location of tension roller 38, whereby the ribbon is peeled from the surface of the now-polymerized mountant and gathered on the take-up spool 41. The now-exposed surface of the mountant encapsulating tissue specimen 5 is essentially optically smooth and planar, since defined by ribbon 33. However, any slight excess of mountant expressed from between ribbon 33 and microscope slide 3 as well as any of the protective layer carried on the surfaces of the slide are unreacted, inasmuch as polymerization thereof has been inhibited by exposure to oxygen in the atmosphere. Subsequently, each microscope slide 3 is passed onto a second ramp arrangement as defined by guides 55. The microscope slide 3 is fed gravitationally onto a moving parallel belt assembly comprising belts 61 and 63. Belts 61 and 63 are trained over shoulders defined at opposite ends of a suitably driven roller 65 and a corresponding idler roller 67, the central surface portions of each being preferably recessed. Preferably, the driven roller 65 is actuated by microswitch 29, with suitable delay, concurrently with the delivery of a microscope slide 3.

Wash station 13 includes a chamber 69 comprising openings disposed on opposite wall portions 71 and 73 for accomodating the endless belts 61 and 63. Portions 75 of guides 55 maintain the orientation of the microscope slide 3 on belts 61 and 63, during passage through chamber 69 on belts 61 and 63. An appropriate washing fluid, for example, Freon TF, for removing unreacted mountant from the surfaces of microscope slide 3 is supplied from container 77. Although not illustrated, container 77 also includes a positive displacement pump, which is energized by microswitch 29 concurrently with driven roller 65. The outlet of such pump is connected to conduit 79, which is connected to two branch conduits 81 and 83. The outlets of branch conduits 81 and 83 are arranged to direct the pumped wash fluid over the lower and upper surfaces, respectively, of each microscope slide 3 as it is passed through chamber 69. Preferably, the outlets of branch conduits 81 and 83, respectively, are structured to direct a spray substantially normal to the lower and upper surfaces of the microscope slide 3 being passed therethrough. The wash liquid is subsequently collected at the bottom of chamber 69 and passed along drain 85 and conduit 87 to container 77 for recirculation.

As a microscope slide 3 emerges from chamber 69, it is carried by belts 61 and 63 between blowers 88 and 89, which have been energized concurrently with driven roller 65 and the pump contained within container 77. Blowers 88 and 89 are disposed to direct warm air over opposite surfaces of the microscope slide 3, to effectively evaporate any residual wash liquid remaining thereon. At this time, the mounting of the tissue specimen 5 on such microscope slide 3 has been completed, and the slide is immediately available for examination.

Subsequent to the drying process, the microscope slide 3 is passed from belts 61 and 63 into a stacking arrangement 17. Stacking arrangement 17 comprises a bin 91 provided with an integral ramp 93 for receiving microscope slides 3 passed, in turn, from belts 61 and 63. The end of guides 55 cooperate with ramp 93 in maintaining proper orientation of such slides. Bin 91 is provided a false bottom 97 supported on a spring 99, for minimizing the drop of the microscope slides 3, directed thereto. Preferably, bin 91 is a four-sided structure, two wall sections having been removed to illustrate the stacking of the accumulated microscope slides 3. Inasmuch as the mountant encapsulating the tissue specimen 5 on each microscope slide 3 has been fully reacted and dried, such immediate stacking of such slides does not affect the optical properties thereof nor cause them to stick together.

As the apparatus of FIG. 1A has been described with respect to mounting of tissue specimens on microscope slides on a discrete basis, it is evident that the components, above described, which are controlled by microswitch 29 are operative for a time sufficient to process the individual microscope slides as they are passed through the apparatus. Of course, it would be evident that each of these same components could be operated on a continuous basis for the mounting of tissue specimens which are directed successively and automatically along feeding arrangement 11.

While the presently preferred embodiment of the invention has been illustrated and described, it is apparent to those skilled in the art that the apparatus and method are susceptible to various changes and details without departing from the principles thereof.

What is claimed is:

1. A system for preparing a plurality of specimens affixed to transparent carriers comprising:
   (a) a plurality of transparent carriers each having a first surface facing in the same direction;
   (b) a plurality of discrete thin biological cellular specimens;
   (c) said biological cellular specimens being affixed to said first surface of said transparent carriers;
   (d) means adapted and constructed when said system is operated to move said transparent carriers sequentially along a pre-determined path and to expose at least that portion of said first surface having said affixed specimens;
   (e) means operatively disposed for bathing the specimen with a volatile solvent containing a low concentration of a polymerizable material.
   (f) a further source of liquid polymerizable material, said polymerizable material being transparent when polymerized;
   (g) means further disposed along said path and adapted and constructed when said system is operated to supply material from said source subsequent to evaporation of said volatile solvent sequentially onto each of said specimens on said first surface of said plurality of transparent carriers and in sufficient quantity to encapsulate said each specimen;
   (h) an optically smooth oxygen impermeable continuous elongate planar member;
   (i) means further disposed along said path adapted and constructed when said system is operated to sequentially sandwich said specimen between said first surface of said transparent carrier and said planar member;
   (j) means further disposed along said path adapted and constructed when said system is operated to expose said polymerizable material to ultra-violet light subsequent to being sandwiched, so as to polymerize said polymerizable material disposed between said planar member and said corresponding surfaces of said transparent carriers;
   (k) means adapted and constructed when said system is operated to part said planar member from said transparent carriers;

2. The system of claim 1, including means further disposed along said path adapted and constructed when said system is operated to wash sequentially said transparent carriers whereby to remove any unpolymerized material.

3. The system of claim 2, including means further disposed along said path adapted and constructed when said system is operated to dry sequentially said transparent carriers subsequent to washing.

4. The system of claim 3 including means further disposed along said path adapted and constructed when said system is operated to accumulate sequentially each of said plurality of transparent carriers subsequent to drying.

* * * * *